United States Patent [19]

Morris

[11] Patent Number: 4,532,645
[45] Date of Patent: Jul. 30, 1985

[54] QUICK RELEASE AND ADJUSTABLE COLLIMATOR DEVICE

[75] Inventor: William W. Morris, Woodstock, Ill.

[73] Assignee: X-Cel X-Ray Corporation, Crystal Lake, Ill.

[21] Appl. No.: 536,536

[22] Filed: Sep. 28, 1983

[51] Int. Cl.³ .............................................. F16M 9/00
[52] U.S. Cl. .................................... 378/147; 378/205; 248/674; 248/676; 411/539
[58] Field of Search ............... 378/147, 148, 205, 149, 378/150, 151, 152, 153; 248/674, 676; 411/539

[56] References Cited

U.S. PATENT DOCUMENTS

| | | | |
|---|---|---|---|
| 2,307,612 | 1/1943 | Westendorp | 378/147 |
| 4,250,388 | 2/1981 | Janu | 378/205 |
| 4,302,675 | 11/1981 | Wake et al. | 378/150 |

*Primary Examiner*—Alfred E. Smith
*Assistant Examiner*—Charles F. Wieland
*Attorney, Agent, or Firm*—Marshall, O'Toole, Gerstein, Murray & Bicknell

[57] ABSTRACT

The invention disclosed and claimed herein relates generally to a new and improved X-ray beam apparatus having an adjustable collimator device and more particularly to an X-ray apparatus in which the collimator device can be readily removed from the X-ray tube device of the apparatus and relatively easily adjusted relative to the X-ray tube device.

11 Claims, 5 Drawing Figures

QUICK RELEASE AND ADJUSTABLE COLLIMATOR DEVICE

BACKGROUND OF THE INVENTION

In the manufacture and use of X-ray systems, particularly for diagnosis and treatment of the human body, the X-ray apparatus generally available provides a beam of X-radiation which impinges upon a subject in a desired specific location. Various X-ray apparatus systems are available in the prior art as exemplified, for example, in U.S. Pat. Nos. 3,156,824; 3,304,427 and 3,448,270. Generally, these units utilize an X-ray tube device having a collimator device mounted to it. The collimator device has a shutter system comprising a plurality of adjustable shutter elements, the shutter elements being adapted for adjustment in overlying relationships with each other to provide a desired aperture defined by the ends of the shutter elements thereby regulating or controlling the size and shape of the beam of x-radiation on a particular object.

It has been found that it becomes necessary to service the collimator devices mounted in the X-ray apparatus. Moreover, it is desired to be able to readily adjust the collimator unit relative to the center line of the X-ray beam which is emitted from the X-ray tube in the X-ray device. Unfortunately, it has been found that it is difficult both in time and cost to service conventional units because the collimator devies are mounted on the X-ray tube device of the X-ray apparatus in a manner that requires an inordinate amount of time to attach or remove the collimator device with respect to the X-ray device. In some instances where it is necessary to return the collimator unit to the factory for appropriate service or repair work, it has been found that some collimator devices presently available are not suited to relatively quick release from the X-ray device such that a difficult, time consuming and costly operation is involved in removing the collimator device from the X-ray device.

Further, it has been found that, in some instances, it is desirable to move or adjust the collimator device relative to the X-ray portion of the apparatus, it being particularly desired to be able to achieve this movement in a manner which is convenient and not particularly time consuming to a service or other person normally responsible for making such adjustments.

SUMMARY OF THE INVENTION

The present invention serves to obviate the above-mentioned problems associated with conventional X-ray apparatus having collimator units or devices attached to the X-ray device of the apparatus. The X-ray apparatus disclosed and claimed herein employs a collimator device which can readily be disassembled from the X-ray portion or device of the apparatus. Further, the apparatus of the present invention permits the collimator unit to be relatively readily and easily adjusted whereby the shutter element assembly is readily positioned in a particular location relative to the X-ray tube device.

Briefly, the invention of the present invention comprises the mounting of the elements forming the collimator unit upon a collimator base member which seats against upon the outer surface of a frame base of the X-ray tube device. A movable subplate seats against the inner surface of the frame plate of the X-ray tube device. Suitable first mounting means mount the collimator unit to the subplate whereby upon release or loosening of the first mounting means, the collimator unit can be readily assembled to or disassembled from the X-ray tube portion of the apparatus.

Further, second mounting means serve to mount the releasable subplate to the X-ray tube device frame plate. Upon release or loosening of the second mounting means, the subplate can be moved relative to the X-ray tube device frame plate such that upon assembly of the collimator unit to the subplate, the collimator unit and its shutter elements will be located in a new, desired position relative to the X-ray tube portion of the apparatus.

A better understanding of the invention will be seen and understood from the various drawings and detailed description.

DETAILED DESCRIPTION

Figure 1:
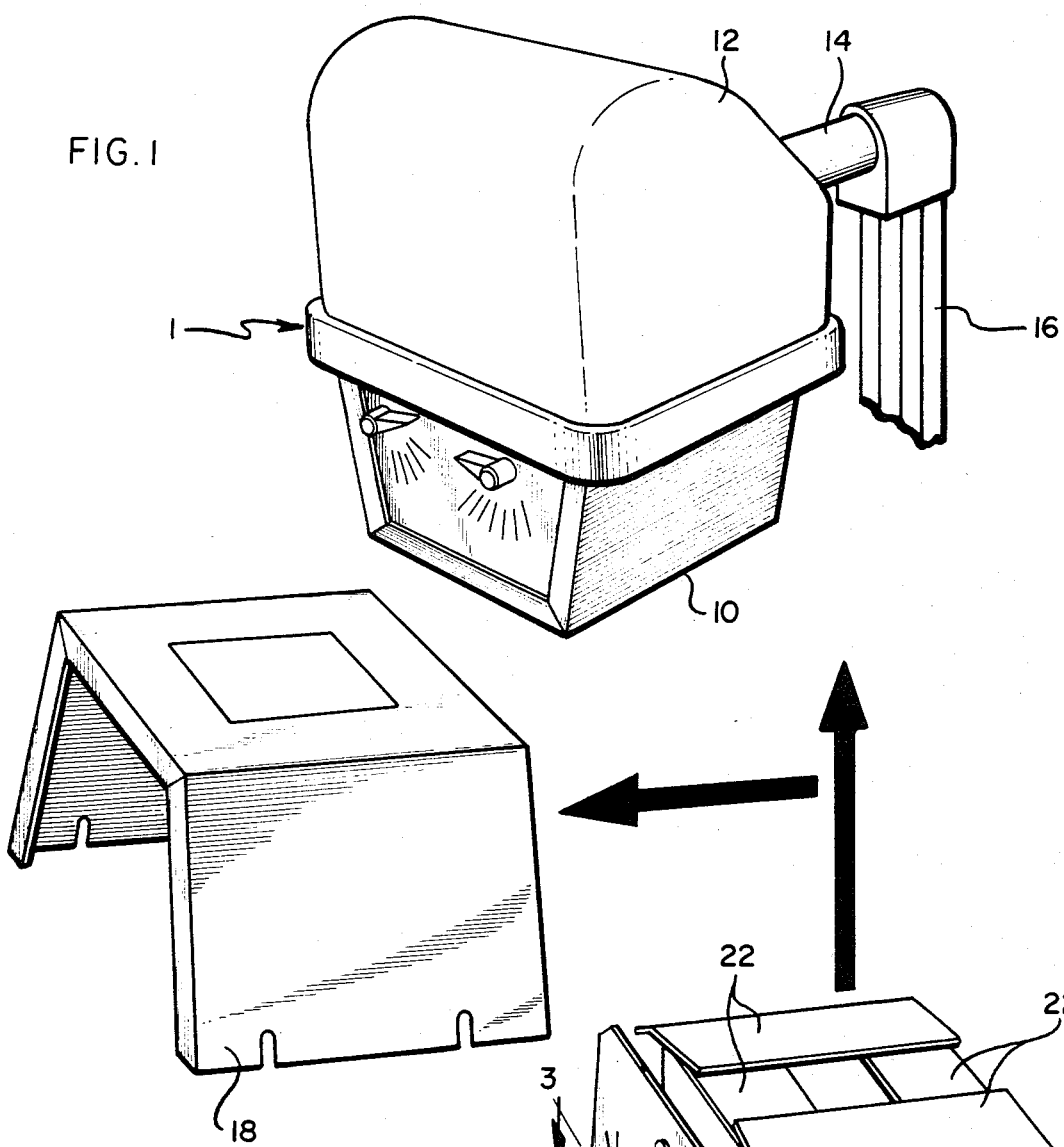
FIG. 1 shows a fragmentary, perspective view of the X-ray apparatus having an X-ray tube device or portion and collimator device or unit attached to the X-ray tube device, with the apparatus being disposed in a normal, operative position.

Referring to the drawings and particularly FIG. 1, there is shown an X-ray apparatus 1 comprising a collimator device 10 which is mounted upon and depends from an X-ray tube device 12. X-ray device 12 is connected to a mounting arm 14 which in turn is fastened for rotation of 180° to stand 16. X-ray device 12 is adapted to be rotated 180° which is desired in the instance where servicing of the collimator device 10 is required. Shroud 18 is removed from device 10 by loosening shroud screws 20 whereby the elements of collimator unit 10 such as adjustable shutter elements 22 are exposed.

Figure 2:
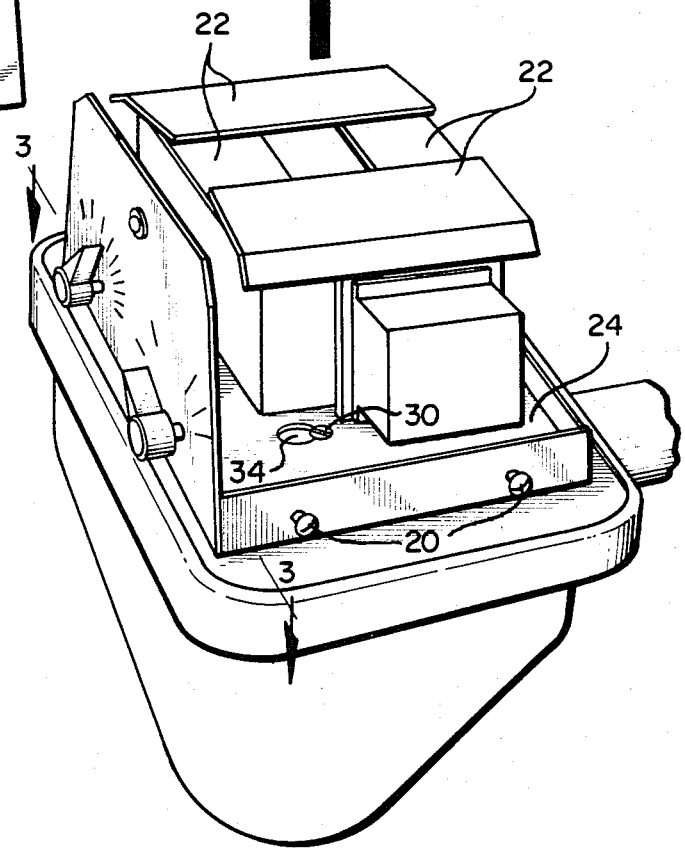
FIG. 2 shows the X-ray apparatus of FIG. 1 rotated 180° with the collimator device shroud removed and the elements of the collimator unit exposed and seated on the X-ray tube portion of the apparatus.
Figure 3:
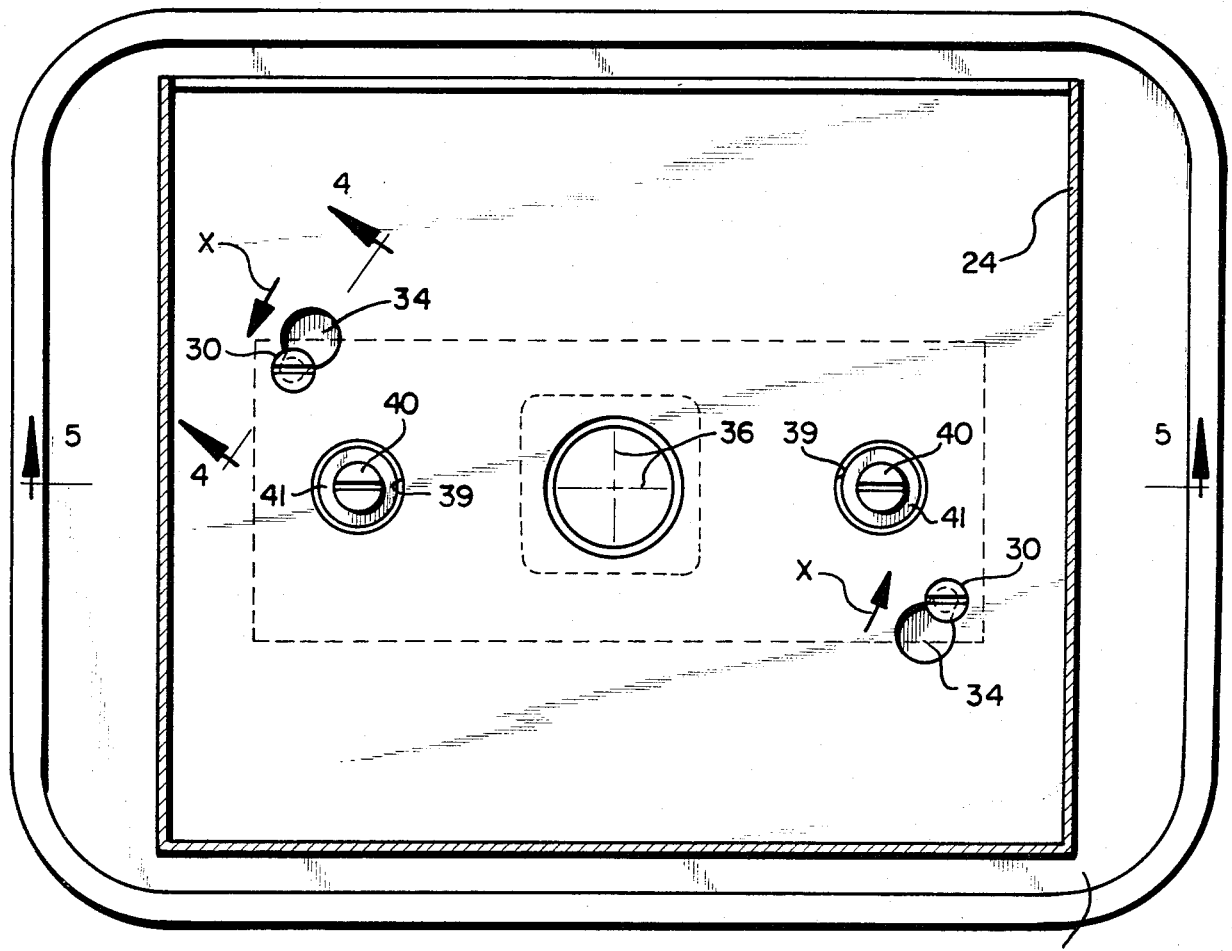
FIG. 3 shows a fragmentary section view taken along lines 3—3 in FIG. 2 with the elements of the collimator unit removed for clarity except for the collimator unit base member which is seated upon the outer surface of the frame base of X-ray tube device.
Figure 4:
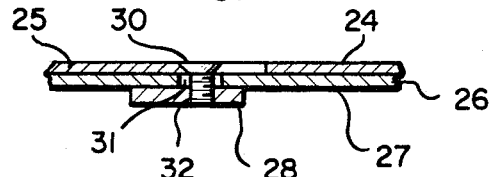
FIG. 4 shows a fragmentary, section view taken along lines 4—4 in FIG. 3 showing a first screw mounting means connecting the collimator base member to a movable subplate with the X-ray tube device frame base disposed therebetween; and, FIG. 5 shows a fragmentary section view taken along lines 5—5 in FIG. 3 showing a second screw mounting means which connects the subplate to the X-ray tube device frame base whereby the subplate can be moved relative to the frame base.

It will be observed that the elements forming the collimator device are disposed upon a collimator unit base member 24 shown in FIG. 2; however, these elements are shown removed from the base member 24 in FIG. 3 so as to expose base member 24. Base member 24 is adapted to seat against the outer surface 25 of X-ray tube device frame base 26.

A movable subplate 28 is seated against the inner surface 27 of frame base 26. A first mounting means in the form of screws 30 serve to lock collimator unit base member 24 on frame base 26. Screws 30 extend through corresponding openings 31 in frame base 26 and are threaded into threaded hole 32 in subplate 28 thereby locking collimator unit base member 24 on frame base 26.

When it is desired to remove collimator device 10 from unit X-ray device 12, screws 30 are loosened and base member 24 is turned as indicated by the arrows "X" in FIG. 3 so that openings 34 are aligned with the heads of screws 30 whereupon collimator device 10 can be lifted off of frame base 26. The collimator device can be assembled upon the X-ray device merely by following the reverse of the disassembly procedure outlined above. Upon reassembly of the collimator device following removal for servicing or the like, the collimator is reseated on frame base 26 in the same position that it was located prior to its removal from frame base 26. This ability to replace the collimator device so that it will be in the same position as it was before removal from base 26 gives a desired repeatability within reasonable accuracy which is desirable and important with respect to the X-ray apparatus as disclosed in this application.

Utilizing this assembly and disassembly procedure offered by the present invention permits a service person to quickly and easily remove collimator device 10 from the X-ray tube device 12. While the conventional, electrical connections between the devices 10 and 12 have not been shown, it has been found that conventional disconnects allow the wiring and other electrical connections to be readily connected and disconnected. Inasmuch as electrical disconnects are readily available, they would be obvious to a person of ordinary skill in the art and form no part of the present invention.

Figure 5:
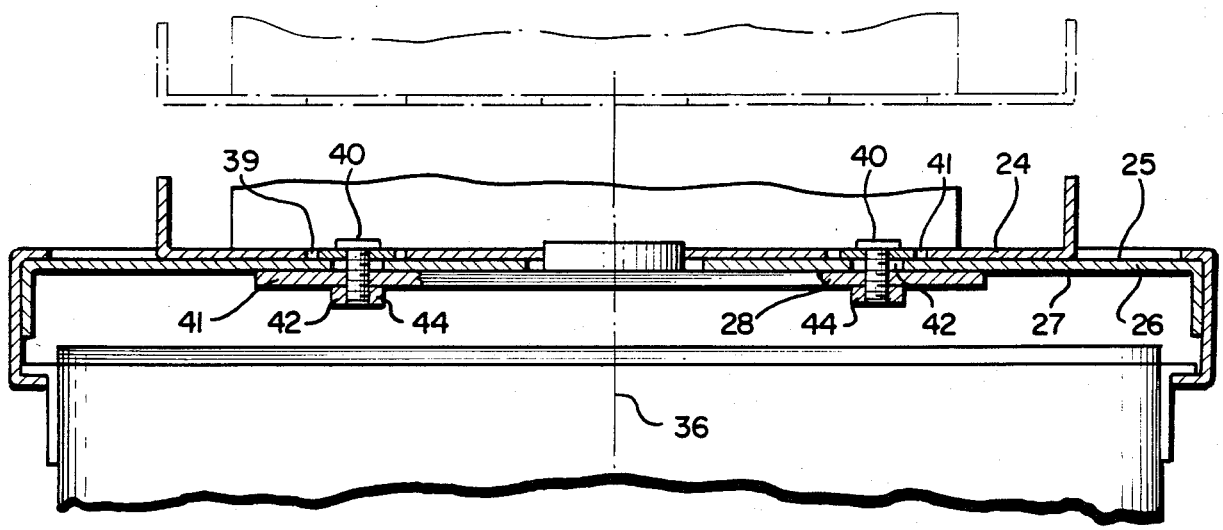

In some instance it is desired to adjust the position of collimator device 10 relative to the normal center lines 36 of the X-ray beam emitted from X-ray device 12. This adjustment can be achieved with the present device by moving subplate 28 relative to frame base 26. Referring to FIGS. 3 and 5, it will be observed that a second mounting means in the form of threaded fasteners 40 are utilized to mount or seat subplate 28 on the inner surface 27 of base frame 26. Each fastener 40 passes through washer 41. Washer 41, as shown in FIG. 5, is seated on the outer surface of frame base 26. Fastener 40 extends through an opening 42 in frame base 26 and is threaded into a press nut 44 fixed to the outer surface of subplate 28.

When it is desired to adjust the position of collimator device 10 relative to X-ray tube device 12, screws 40 are loosened and collimator device base member 24 can be moved in any desired direction as permitted by the size of the opening 39 in base member 24 which is larger in diameter than the diameter of washers 41. Further opening 42 in frame base 26 is larger than the diameter of fastener 40 to permit fastener 40 to move within the opening 42. By moving the collimator device to a new location, the shutter elements 22 will be repositioned, as desired, relative to X-ray unit center lines 36. Once the desired adjustment has been made and subplate 28 has been moved relative to frame base 26, screws 40 are tightened. When collimator device 12 then is fastened to subplate 28 by first mounting means 30, the collimator device will be located and locked in its reoriented position relative to center lines 36.

It will be understood that the invention disclosed and claimed herein can be embodied in modified forms, and is not limited to the exact details as shown and described.

What is claimed:

1. An X-ray apparatus comprising a collimator device connected to an X-ray tube device having a frame base;
   said frame base having an inner surface and an outer surface;
   said collimator device including a base member which is releasably mounted on the outer surface of said frame base;
   a subplate means mounted to the inner surface of said frame base;
   said subplate and frame base being adjustably connected to each other;
   said subplate means being free of contact with said base member whereby said frame base is disposed between said collimator base member and said subplate means;
   said base member is removable from said frame base free of interference with said subplate; and,
   first mounting means for releasably connecting said collimator base member to said subplate;
   whereby said collimator device is removable from said frame base.

2. An X-ray apparatus in accordance with claim 1 wherein said first mounting means comprises a screw means which passes through said base member and is threaded into said subplate.

3. An X-ray apparatus in accordance with claim 2 wherein said frame base includes an opening through which said screw means pass.

4. An X-ray apparatus in accordance with claim 1 wherein said subplate is releasably secured to said frame base.

5. An X-ray apparatus in accordance with claim 4 wherein said subplate is releasably seated against said inner surface of said frame base by means of a second mounting means.

6. An X-ray apparatus in accordance with claim 5 wherein said second mounting means includes a screw means and a washer means, said screw means being seated on said washer means; said washer means being disposed in an enlarged opening in said base member, and said second screw means being fastened to said subplate.

7. An X-ray apparatus in accordance with claim 6 wherein said opening in said base member is adapted to receive said washer means is larger in size than said washer means and said second screw means passes through an opening in said frame base which is larger in size than the size of said second screw means.

8. An X-ray apparatus comprising a collimator device connected to an X-ray device having a frame base;
   said frame base having an inner surface and an outer surface;
   said collimator device including a base member which is releasably mounted on the outer surface of said frame base;
   a subplate mounted on the inner surface of said frame base;
   said subplate and frame base being adjustably connected to each other;
   said subplate being free of contact with said base member whereby said frame base is disposed between said collimator base member and said subplate and said base member is removable from said frame base free of contact with said subplate; and,
   first mounting means for releasably connecting said collimator base member to said subplate;

whereby said collimator device is removable from said frame base without first removing said subplate.

9. An X-ray device apparatus in accordance with claim 8 wherein said apparatus includes a second mounting means for releasably adjusting said subplate on said inner surface relative to said frame base.

10. An X-ray apparatus in accordance with claim 9 wherein said first mounting means comprise screw means which pass through an enlarged opening in said base member and is threaded into said subplate.

11. An X-ray apparatus in accordance with claim 10 wherein said second mounting means includes a screw means and a washer means, said screw means being seated on said washer means, said washer means being disposed in an enlarged opening on said base member, and said second screw means being fastened to said subplate.

* * * * *